United States Patent
Cordier et al.

(10) Patent No.: US 6,893,152 B2
(45) Date of Patent: May 17, 2005

(54) METHOD AND DEVICE FOR EVALUATING A FUEL GAS WOBBE INDEX

(75) Inventors: Rémy Cordier, Sceaux (FR); Laurent Lantoine, Herblay (FR)

(73) Assignee: Gaz de France, Paris (FR)

( * ) Notice: Subject to any disclaimer, the term of this patent is extended or adjusted under 35 U.S.C. 154(b) by 0 days.

(21) Appl. No.: 10/451,726

(22) PCT Filed: Dec. 20, 2001

(86) PCT No.: PCT/FR01/04125

§ 371 (c)(1),
(2), (4) Date: Oct. 15, 2003

(87) PCT Pub. No.: WO02/052258

PCT Pub. Date: Jul. 4, 2002

(65) Prior Publication Data

US 2004/0062290 A1 Apr. 1, 2004

(30) Foreign Application Priority Data

Dec. 26, 2000 (FR) .............................. 00 17048

(51) Int. Cl.⁷ .......................... G01F 1/00; G01K 17/06
(52) U.S. Cl. ........................ 374/40; 374/43; 374/142; 374/117; 73/1.35; 73/23.2; 73/861
(58) Field of Search ............................ 374/40, 45, 117, 374/118, 119, 142, 143, 138, 159, 43, 54, 36; 73/1.34, 1.25, 1.26, 1.02, 1.35, 23.2, 861

(56) References Cited

U.S. PATENT DOCUMENTS

| | | | | |
|---|---|---|---|---|
| 3,604,254 A | * | 9/1971 | Sabuda ........................ 73/118.1 |
| 4,145,922 A | * | 3/1979 | Estrada et al. ................. 374/39 |
| 4,380,400 A | * | 4/1983 | Searle ........................... 374/37 |
| 4,382,698 A | * | 5/1983 | Szonntagh ..................... 374/37 |
| 4,384,792 A | * | 5/1983 | Sommers et al. .............. 374/36 |
| 4,489,592 A | * | 12/1984 | Pacanowski et al. ........ 73/24.05 |
| 4,810,100 A | * | 3/1989 | Shavit et al. .................. 374/40 |
| 4,823,591 A | * | 4/1989 | Lewis ......................... 73/1.26 |
| 4,881,185 A | * | 11/1989 | Murakami et al. ........... 702/130 |
| 4,941,345 A | * | 7/1990 | Altemark et al. ............. 73/23.2 |
| 5,267,467 A | * | 12/1993 | Caron ......................... 73/1.26 |
| 5,415,024 A | * | 5/1995 | Proffitt et al. ............... 73/61.44 |
| 5,482,679 A | * | 1/1996 | Dijkstra et al. ............... 422/94 |
| 5,635,626 A | * | 6/1997 | Hammond et al. ........... 73/23.2 |
| 5,807,749 A | * | 9/1998 | Hornemann ................. 436/143 |
| 6,047,589 A | * | 4/2000 | Hammond et al. ......... 73/24.01 |
| 6,371,147 B1 | * | 4/2002 | Philippe ........................ 137/6 |
| 6,442,996 B1 | * | 9/2002 | Thurston et al. ........... 73/24.01 |
| 6,446,487 B1 | * | 9/2002 | Van Wesenbeeck et al. . 73/23.2 |
| 6,490,908 B2 | * | 12/2002 | Schley ......................... 73/23.2 |
| 6,517,237 B1 | * | 2/2003 | Hammond et al. ........... 374/31 |
| 6,539,775 B2 | * | 4/2003 | Driftmeier .................. 73/23.2 |

FOREIGN PATENT DOCUMENTS

| | | |
|---|---|---|
| DE | 41 18 781 A1 | 12/1992 |
| EP | 0 469 649 A2 | 2/1992 |
| FR | 2 792 415 | 10/2000 |
| JP | 06148106 A * 5/1994 | .......... G01N/25/26 |
| JP | 2004026611 A * 1/2004 | ............. C01B/3/38 |

* cited by examiner

*Primary Examiner*—Gail Verbitsky
(74) *Attorney, Agent, or Firm*—Leydig, Voit & Mayer, Ltd.

(57) ABSTRACT

A method for evaluating the Wobbe index of a fuel gas belonging to a family of gases. The method includes measuring mass flow rates the fuel gas and of a reference gas, which is not necessarily a fuel gas at respective absolute pressures and temperatures and in a sonic flow through a microjet. An evaluation of the Wobbe index (W) of the fuel gas as W=A×Y+B uses the results of measurements of the fuel gas and the reference gas and is established for all the gases of the family considered.

15 Claims, 1 Drawing Sheet

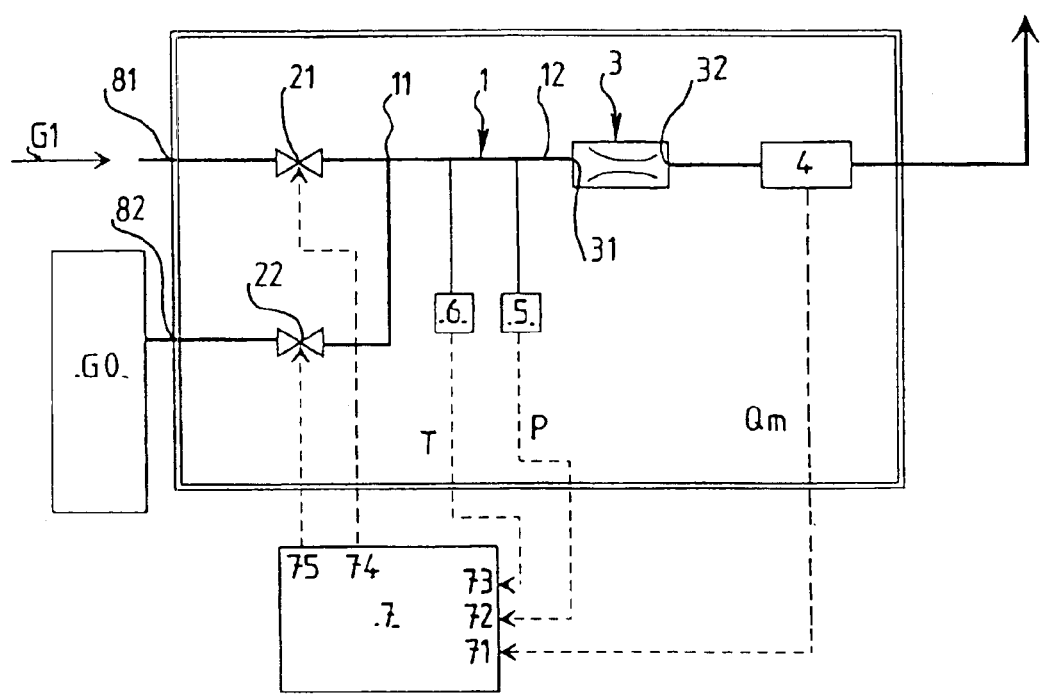

METHOD AND DEVICE FOR EVALUATING A FUEL GAS WOBBE INDEX

FIELD OF THE INVENTION

The invention concerns, in general, the field of techniques for measuring the Wobbe index, which is represented by the ratio of the caloric power of a fuel gas over the square root of the density of this gas.

More specifically, the invention, according to one of its aspects, concerns a method for the evaluation of the Wobbe index of a fuel gas belonging to a gas family which is defined by constituents of a given chemical nature intervening in variable relative proportions, where this method comprises a measurement procedure during which a measurement of the flow rate of this fuel gas is carried out.

BACKGROUND OF THE INVENTION

The Wobbe index constitutes the principal magnitude which is characteristic of a gaseous fuel and, in that quality, it intervenes in the regulations of the combustion of gas burners.

Thus, all other things being the same, the heat flow rate of a burner is proportional to the Wobbe index, and its excess of air directly depends on it.

Since the networks for the transport and distribution of natural gas are becoming increasingly linked, and since they are supplied by a variety of energy sources, the Wobbe index of a gas of a given type can vary within non-negligible proportions, for example, ±5% at a given point of a network.

However, certain industrial methods, particularly in the glass and lime industries, are sensitive to these variations to the point that they require the use of specific combustion regulation solutions, one of these solutions consisting in incorporating the result of a local measurement of the Wobbe index in the regulation algorithms.

To date, all the apparatuses for measuring the Wobbe index which are available on the market are still relatively complex and consequently expensive.

Three principles are known to determine the Wobbe index.

The first principle consists in associating a measurement of the caloric power, obtained by calorimetry or chromatography, with a measurement of density, obtained by densitometry or by chromatography.

The second principle consists in analyzing the products of the combustion of the gas concerned in a small furnace where a sample of this gas is burned stoichiometrically or with an excess of air.

The third principle consists in measuring the physical characteristics of the gas, such as viscosity, heat capacity, etc., and in making a correlation between these measurements and the Wobbe index.

Two examples of the third principle are described in the patent documents DE-41 18 781 and U.S. Pat. No. 4,384,792.

The document DE-41 18 781 indeed describes a method whose purpose is to provide other measurements in addition to that of the Wobbe index, having recourse to two correlation functions with four constants, using three measurements of flow rate, one measurement of differential pressure and one measurement of temperature, and requiring a calibration with methane.

The document U.S. Pat. No. 4,384,792 describes a method for measuring the Wobbe index, having recourse to a correlation function with three constants, using a measurement of volume flow rate, a measurement of differential pressure and a measurement of temperature, and requiring a pressure regulator and a calibration by means of a hydrogenated gas.

These known techniques thus present a relatively high level of complexity, and the purpose of the invention is to propose a method for measuring the Wobbe index, which is easier to carry out, and in addition, a device which is substantially less complex and less expensive than the known devices.

SUMMARY OF THE INVENTION

For this purpose, the method of the invention comprises: an operation supplying, as a measurement of the flow rate of the fuel gas, a measurement of a mass flow rate of this fuel gas in a sonic flow through a fluid restriction, such as an orifice or a microjet, which operation is carried out at an absolute measurement pressure and at an absolute measurement temperature; a calibration method during which a measurement of a mass flow rate of a reference gas in a sonic flow through the fluid restriction is carried out, at an absolute reference pressure and at an absolute reference temperature; and a method of evaluation during which the Wobbe index receives a value which is connected, by means of an empirical affine law which was preestablished for the gas family, to the product of three factors, the first factor representing the ratio of the measurement of the mass flow rate of the fuel gas to the measurement of the mass flow rate of the reference gas; the second factor representing the ratio of the respective images of the absolute reference pressure and the absolute reference measurement by a predetermined polynomial function; and the third factor representing the square root of the ratio of the absolute measurement temperature and the absolute reference temperature.

In the case where the fuel gas and the reference gas can have different pressures, the measurement procedure comprises a measurement of the absolute measurement pressure, and the calibration method comprises a measurement of the absolute reference pressure.

If the absolute measurement pressure and the absolute reference pressure are maintained within a predetermined range, the polynomial function is comparable to the identity function, the image of a pressure (P) by the determined polynomial function thus assuming the form:

$$F(P)=P.$$

In the opposite case, the image of a pressure (P) by the determined polynomial function preferably is of the form:

$$F(P)=P-k \cdot P^{(1-r)}$$

where k and r are construction parameters of the fluid restriction.

In the case where the fuel gas and the reference gas can have different temperatures, the measurement procedure comprises a measurement of the absolute measurement temperature, and the calibration procedure comprises a measurement of the absolute reference temperature.

Under these conditions, the reference gas can be freely chosen from a group of gases comprising nonfuel gases and gaseous mixtures, such as air or nitrogen.

The method of the invention advantageously comprises a preliminary correlation procedure during which the empirical affine law is established for at least two gases of the family of gases.

For the evaluation of the Wobbe index of a gas belonging to the family of natural gases, the empirical affine law is defined by an ordinate at the origin equal to −18.40.

In this case, and if compressed air is used as the reference gas, the empirical affine law is defined by a slope equal to 19.40.

If, on the other hand, nitrogen is used as a reference gas, the empirical affine law is defined by a slope equal to 19.72.

However, still concerning the evaluation of the Wobbe index of a gas belonging to the family of natural gases, if methane is used as the reference gas, the empirical affine law is defined by a slope equal to 33.28.

The invention also concerns a device for carrying out the method for evaluating the Wobbe index as described above, where this device is characterized in that it comprises a tube presenting an inlet and an outlet, admission means for selectively guiding to the inlet of the pipe a flow of fuel gas under pressure or a flow of reference gas under pressure, a fluid restriction, such as an orifice or a microjet, presenting an inlet which is connected to the outlet of the pipe, and an outlet, and a mass flow rate metering device which is connected to the output of the fluid restriction and delivers an output signal which is representative of the mass flow rate of the gas which flows through this fluid restriction in a sonic flow.

In the case where the reference gas and the fuel gas can be used under different conditions of pressure and/or temperature, the device of the invention comprises an absolute pressure sensor and/or an absolute temperature sensor installed on the pipe.

The above-mentioned admission means comprise, for example, a first principal inlet for the combustible gas, a second principal inlet for the reference gas, and a first and second electrovalve intercalated between the inlet of the pipe and the first and second principal inlets, respectively.

In this case, the device of the invention is advantageously equipped with a logic unit comprising at least three acquisition inputs which are respectively connected to the flow rate metering device, the pressure sensor and the temperature sensor, and two control outputs connected to the electrovalves, respectively.

BRIEF DESCRIPTION OF THE DRAWING FIGURE

Other characteristics and advantages of the invention will become clear in the description made thereof below, for information and in a nonlimiting manner, with reference to the single FIGURE, which consists of a schematic of a device according to the invention.

To make the presentation of the invention more concrete, the present description is first made with reference to the drawing, and to the device which it represents.

This device comprises a pipe 1 whose inlet 11 is connected to a first principal inlet 81 of the device by a first electrovalve 21, and to a second principal inlet 82 of the device by a second electrovalve 22.

The first principal inlet 81 of the device is continuously connected to a pressurized source of the fuel gas to be analyzed G1.

The second principal inlet 82 of the device is permanently connected to a pressurized source of a reference gas G0, such as air, nitrogen or methane, among other possibilities.

The admission means consist of the principal inlets 81 and 82, in combination with the electrovalves 21 and 22, each one of which being controlled so that it allows passage while the other one is closed, thus allowing the transport, at will, up to the inlet 11 of the pipe 1 of a flow of fuel gas G1 under pressure, or a flow of reference gas G0 under pressure.

Moreover, the device comprises a fluid restriction 3 whose inlet 31 is connected to the outlet 12 of the pipe 1, and a mass flow rate metering device 4 which is connected to the outlet 32 of the fluid restriction 3.

The fluid restriction 3, which is intended to be the location of a sonic flow of the gas G0 or G1 which traverses it, and intended to offer resistance to this flow, typically is in the shape of an orifice or a microjet whose diameter is, for example, on the order of 0.4 mm.

The mass flow rate metering device 4, which is known in itself and has a dimension of, for example, approximately 300 normal liters per hour, delivers an output signal Qm which is representative of the mass flow rate of the gas G0 or G1 which traverses the fluid restriction 3 in a sonic flow.

In the embodiment variant which allows the greatest measuring precision, the device of the invention also comprises an absolute pressure sensor 5 and an absolute temperature sensor 6, both installed on the pipe 1, which is arranged so as to deliver measurement signals P and T, which are representative of the pressure and of the temperature, respectively, existing in this pipe; typically the pressure P is less than 5 bar.

The control of the electrovalves 21 and 22, and the exploitation of the signals Qm, P and T, can be entrusted to a logic unit 7, which comprises three acquisition inlets 71, 72, and 73, which are connected to the flow rate metering device 4, the pressure sensor 5 and the temperature sensor 6, respectively, and two control outputs 74 and 75 which are connected to the electrovalves 21 and 22, respectively.

The method of the invention, which is carried out in this device, makes it possible to evaluate the Wobbe index of any fuel gas such as G1, provided that the family of gases to which this gas belongs has been identified, where the family is defined by the principal chemical constituents of this gas, even if they exist in variable proportions, and with the proviso that prior knowledge, to be specified below, on this family of gases is available.

This method comprises the following operations:

First, any one of the gases to be used, for example, the fuel gas G1, is allowed to traverse the restriction 3 in a sonic flow, and the signal Qm1 which is then delivered by the flow rate metering device 4 is taken into account as a measurement of the mass flow rate of the fuel gas G1 in the restriction 3.

Correlatively, the signals P1 and T1 which are delivered over time by the sensors 5 and 6, respectively, are taken into account as measurements of the absolute measurement pressure and the absolute measurement temperature, respectively.

The second one of the gases to be used, in this instance, the reference gas G0, is then allowed to traverse the restriction 3 in a sonic flow, and the signal Qm0 which is then delivered by the flow rate metering device 4 is taken into account as a measurement of the mass flow rate of the reference gas G0 in the restriction 3.

Correlatively, the signals P0 and T0 which are delivered over time by the sensors 5 and 6, respectively, are taken into account as measurements of the absolute reference pressure and the absolute reference temperature, respectively.

This phase of measurement is followed by a phase of evaluation during which at least three factors, which will be noted Za, Zb and Zc, are evaluated.

The first factor Za is represented by the ratio Qm1/Qm0 of the output signals of the flow rate metering device 4 for the gases G1 and G0, that is, by the ratio of the measurement of the mass flow rate Qm1 of the fuel gas G1 to the measurement of the mass flow rate Qm0 of the reference gas G0.

The second factor Zb is represented by the ratio $F(P0)/F(P1)$ of the image $F(P0)$ of the absolute reference pressure P0 by a determined polynomial function F, which will be specified below, to the image $F(P1)$ of the absolute measurement pressure P1 by the polynomial function F.

In practice, if the pressures P0 and P1 are close, for example, if between them there is only a maximum relative difference on the order of 2–3%, the polynomial function F is considered equal to the identity function, that is, the ratio $F(P0)/F(P1)$ simply can be considered equal to the ratio $P0/P1$.

The third factor Zc is represented by the square root $(T1/T0)^{1/2}$ of the ratio $T1/T0$ of the absolute measurement temperature T1 to the absolute reference temperature T0.

Under these conditions, the method of the invention assigns to the fuel gas G1, as Wobbe index, the value W defined by an empirical affine law of the form:

$$W = A \times Y + B,$$

in which the term Y represents the product $Za \times Zb \times Zc$ of the three factors Za, Zb and Zc, and in which the coefficient A, called the "slope," and the coefficient B, called the "ordinate at the origin," are pre-established, for the gases belonging to the family of gases considered, in a manner which is specified below.

If the device comprises means which make it possible to make P1 equal to P0, and T1 equal to T0, that is, if:

$$(P0/P1) = 1 \text{ and } (T1/T0)^{1/2} = 1,$$

the factor Za can be considered directly equal to the term Y, as shown easily from the above relations, and the fact that the factors Zb and Zc are then both equal to 1.

In the case where the pressures P0 and P1 are different from each other, and they present, for example, between themselves a relative difference which is greater than 3%, one can no longer consider the polynomial function F equal to the identity function, that is, the image $F(P)$ of a pressure P by this function F can no longer be considered equal to the pressure P itself, but it must be corrected by a factor noted $C_D$ equal to $1 - k \cdot P^{-r}$.

The factor noted $C_D$ indeed makes it possible to take into the account the effect which the boundary layer has, due to the viscosity of the gas which traverses the restriction 3, on the flow characteristics of this gas, where the parameters k and r which occur in the factor $C_D$ are construction parameters of the fluid restriction 3, which can either be supplied by the manufacturer of this restriction, or they can be determined by techniques which are well known to a person skilled in the art.

In a special example of an embodiment of the invention, the factor $C_D$ for a given restriction was set equal to $1 - 0.881 \cdot P^{-4.9}$.

Regardless of the particular values of k and r, the image of a pressure P by the polynomial function F thus is of the form:

$$F(P) = P - k \cdot P^{1-r},$$

and the second factor Zb, which is represented by the ratio $F(P0)/F(P1)$, takes the form:

$$Zb = (P0 - k \cdot P0^{1-r})/(P1 - k \cdot P1^{1-r}).$$

In the case of the evaluation of the Wobbe index of a gas belonging to the family of the natural gases, the ordinate at the origin B of the empirical affine law $W = A \times Y + B$ assumes the value $-18.40$.

Moreover, if, for the same application, compressed air is used as the reference gas G0, the slope A of the empirical affine law $W = A \times Y + B$ assumes the value 19.40, where this law is thus defined overall by the relation:

$$W = 19.40 \times Y - 18.40,$$

that is, also by:

$$W = 19.40 \times Za \times Zb \times Zc - 18.40.$$

In the case of the evaluation of the Wobbe index of a gas belonging to the family of the natural gases, and the use of nitrogen as reference gas G0, the slope A of the empirical affine law $W = A \times Y + B$ assumes the value 19.72, where this law is thus defined overall by the relation:

$$W = 19.72 \times Y - 18.40,$$

that is, also by:

$$W = 19.72 \times Za \times Zb \times Zc - 18.40.$$

In the case of the evaluation of the Wobbe index of a gas belonging to the family of the natural gases, and the use of pure methane as reference gas G0, the slope A of the empirical affine law $W = A \times Y + B$ assumes the value 33.28, where this law is thus defined overall by the relation:

$$W = 33.28 \times Y - 18.40,$$

that is, also by:

$$W = 33.28 \times Za \times Zb \times Zc - 18.40.$$

As shown in the preceding examples, the invention allows the free choice of the reference gas G0, so that it is possible to use, as the reference gas, nonfuel gases and mixtures of gases which consequently are inexpensive, such as air or nitrogen.

In the case of the evaluation of the Wobbe index of the gas belonging to the family of the natural gases and/or the use, as reference gas G0, of a different gas from those for which the empirical affine law $W = A \times Y + B$ was defined above, the method of the invention must include a preliminary correlation procedure, during which the empirical affine law $W = A \times Y + B$ is established for at least two gases G1i of the new family of fuel gases considered, and/or for at least one reference gas G0 such as air, nitrogen or methane, or for another reference gas G00.

This preliminary correlation procedure can be easily carried out, on the one hand, by measuring the factors such as Zai, Zbi, and Zci, respectively obtained for the different combustible gases G1i of the new family of gases with the same reference gas, and on the other hand, by directly measuring, using a different technique than that of the invention, for example, one of the known traditional techniques, the Wobbe indexes, such as Wi of these same fuel gases, and finally by solving, in a manner which is in itself well known, the system of equations of the first degree of the type $Wi = A \times Zai \times Zbi \times Zci + B$ to obtain the values to be assigned to the parameters A and B, which are a priori unknown, and which must be used according to the method of the invention for this new family of gases.

From the physical point of view, the measurement of the mass flow rate Qm for a gas such as G0 or G1, which is carried out under the conditions presented above with reference to the figure, is connected with a quantity called the "normal mass flow rate" and noted Q by the relation:

$$Qm=Q/C,$$

in which C is a correction coefficient which depends on the different physical properties of the actual gas for which the measurement is carried out, and more precisely, on its heat capacity, its viscosity, and its thermal conductivity.

For a gas having a known composition, the correction coefficient C of this gas is connected with the different correction coefficients Cj of its constituents by the relation:

$$(1/C)=\Sigma(Xj/Cj),$$

where the different coefficients Cj are given in tables established by the manufacturers of mass flow meters, and where each Xj represents the volume fraction of the constituent j.

The normal mass flow rate Q itself satisfies the relation:

$$Q=k\times C_D\times C_R\times P/(T\times d)^{1/2}$$

in which:

k is a construction parameter of the restriction 3, which has already been mentioned, $C_D$ is a correction factor of the from $1-k\cdot p^{-r}$, which has already been mentioned, P is the absolute pressure, of the gas considered, as measured by the sensor 5, T is the absolute temperature of the gas considered, as measured by the sensor 6, d is the density of the gas considered, and $C_R$ is the coefficient of the actual gas of the restriction 3, which, for the actual gas which is the object of the measurements, depends only on the ratio γ of the specific heat $C_P$ of this gas at constant pressure, at its specific heat $C_v$ at constant volume, the coefficient $C_R$ being of the form:

$$C_R-(\gamma)^{1/2}\times(2/(\gamma+1))^{((\gamma+1)/2\times(\gamma-1))},$$

where the ratio γ is typically on the order of 0.67 for methane and the natural gases, and 0.69 for air and nitrogen.

Under these conditions, the above relations make it possible to show that:

$$Y=(Qm1/Qm0)\times(C_{D0}/C_{D1})\times(P0/P1)\times(T1/T0)^{1/2},$$

and that:

$$Y=(C0/C1)\times(C_{R1}/C_{R0})\times(d0/d1)^{1/2},$$

where C0 and C1 denote the correction coefficient C for the reference gas G0 and for the fuel gas G1, respectively, where $C_{R1}$ and $C_{R0}$ denote the coefficient of the actual gas of the restriction 3 for the fuel gas G1 and for the reference gas G0, respectively, and where d0 and d1 denote the density of the reference gas G0 and that of the fuel gas G1, respectively.

From a physical point of view, the method of the invention can thus be analyzed as being based on the formulation of an empirical affine law which connects the Wobbe index W of each fuel gas with each one of the above expressions of the term Y.

What is claimed is:

1. A method for the evaluation of the Wobbe index, W, of a fuel gas of a family of gases defined by constituents having a given chemical nature and occurring in variable relative proportions, the method comprising:

measuring a mass flow rate of the fuel gas in a sonic flow through a fluid restriction at an absolute measurement pressure and at an absolute measurement temperature, calibrating by measuring a mass flow rate of a reference gas in a sonic flow through the fluid restriction at an absolute reference pressure and at an absolute reference temperature, and evaluating the Wobbe index W as W=A×Y+B, established for the family of gases where Y is the product of three factors, Za, Zb, and Zc, wherein Za is a ratio of the mass flow rate of the fuel gas to the mass flow rate of the reference gas, Zb is a ratio of respective images of the absolute reference pressure and the absolute measurement pressure by a determined polynomial function, and Zc is the square root of a ratio of the absolute measurement temperature and the absolute reference temperature, and A and B are constant for the family of gases.

2. The method for the evaluation of the Wobbe index according to claim 1, including measuring the absolute measurement pressure and the absolute reference pressure.

3. The method for the evaluation of the Wobbe index according to claim 2, including maintaining the absolute measurement and reference pressures within a range, and wherein the determined polynomial function is the identity function, the image of a pressure by the determined polynomial function thus being F(P)=P.

4. The method for the evaluation of the Wobbe index according to claim 2, wherein the determined polynomial function is $$F(P)=P-k\cdot P_{(I-r)}$$

and k and r are construction parameters of the fluid restriction.

5. The method for the evaluation of the Wobbe index according to claim 1, including measuring the absolute measurement temperature, and the absolute reference temperature.

6. The method for the evaluation of the Wobbe index according to claim 1, including choosing the reference gas from the group of gases consisting of non-fuel gases and gaseous mixtures.

7. The method for the evaluation of the Wobbe index according to claim 1, including a preliminary correlation procedure of establishing the relationship W=A×Y+B for at least two gases of the family of gases.

8. The method for the evaluation of the Wobbe index according to claim 1, wherein, for a gas belonging to the family of natural gases, B is defined by Y=0 and is equal to −18.40.

9. The method for the evaluation of the Wobbe index according to claim 8, including using compressed air as the reference gas, and wherein A is a slope equal to 19.40.

10. The method for the evaluation of the Wobbe index according to claim 8, including using nitrogen as the reference gas and wherein A is a slope equal to 19.72.

11. The method for the evaluation of the Wobbe index according to claim 8, including using methane as the reference gas and wherein A is a slope equal to 33.28.

12. A device for collecting data for determining the Wobbe index of a fuel gas of a family of gases, comprising:

a tube including an inlet and an outlet;

admission means for selectively guiding, to the inlet of the tube, a flow of a fuel gas under pressure or a flow of a reference gas under pressure, the admission means comprising a first principal inlet for the fuel gas, a second principal inlet for the reference gas, and first and second valves intercalated between the inlet of the tube and the first and second principal inlets, respectively;

a fluid restriction having an inlet connected to the outlet of the tube, and an outlet;

a mass flow rate metering device connected to the outlet of the fluid restriction and delivering an output signal representative of the mass flow rate of the gas traversing the fluid restriction in a sonic flow; and a logic unit comprising
at least one acquisition input connected to the flow rate metering device,
two control outputs connected to the valves,
means for piloting the admission means to guide, successively, a first flow of the fuel gas and a second flow of the reference gas to the tube,
means for collecting data issued by the mass flow rate metering device during the first and second flows through the tube, and
means for determining the Wobbe index based on the data collected.

13. The device according to claim 12, comprising an absolute pressure sensor installed on the tube, wherein the logic unit includes, as an acquisition input connected to the absolute pressure sensor, means for collecting data issued by the absolute pressure sensor during the first and second flows, and
means for determining the Wobbe index based on the data collected from the mass flow rate measuring device and from the absolute pressure sensor.

14. The device according to claim 13, comprising an absolute temperature sensor installed on the tube, wherein the logic unit comprises one acquisition input connected to the absolute temperature sensor, and the means for determining the Wobbe index determines the Wobbe index based upon data collected from the absolute temperature sensor.

15. A device for collecting data for determining the Wobbe index of a fuel gas of a family of gases, comprising:

a tube including an inlet and an outlet:

admission means for selectively guiding, to the inlet of the tube, a flow of a fuel alas under pressure or a flow of a reference gas under pressure, the admission means comprising a first principal inlet for the fuel gas, a second principal inlet for the reference gas, and first and second valves intercalated between the inlet of the tube and the first and second principal inlets, respectively;

a fluid restriction having an inlet connected to the outlet of the tube, and an outlet;

a mass flow rate metering device connected to the outlet of the fluid restriction and delivering an output signal representative of the mass flow rate of the gas traversing the fluid restriction in a sonic flow; and an absolute pressure sensor installed on the tube;

an absolute temperature sensor installed on the tube; and a logic unit comprising at least three acquisition inputs connected to the flow rate metering device, the pressure sensor, and the temperature sensor, respectively, and two control outputs connected to the valves, respectively.

* * * * *